（12）United States Patent
Flanagan

(10) Patent No.: US 8,591,230 B2
(45) Date of Patent: Nov. 26, 2013

(54) INTERPROXIMAL NON-SURGICAL CARIES TREATMENT DEVICE AND METHOD

(76) Inventor: Dennis Flanagan, Mansfield, CT (US)

( * ) Notice: Subject to any disclaimer, the term of this patent is extended or adjusted under 35 U.S.C. 154(b) by 0 days.

(21) Appl. No.: 13/506,149

(22) Filed: Mar. 30, 2012

(65) Prior Publication Data

US 2013/0022936 A1  Jan. 24, 2013

Related U.S. Application Data

(60) Provisional application No. 61/572,711, filed on Jul. 20, 2011.

(51) Int. Cl.
*A61C 17/00* (2006.01)
*A61C 17/02* (2006.01)
*A61C 5/04* (2006.01)

(52) U.S. Cl.
USPC .................................. 433/80; 433/89; 433/90

(58) Field of Classification Search
USPC ................. 433/29–31, 81, 224, 215, 216, 80, 433/89–90, 147–149; 604/1–3; 132/320–329
See application file for complete search history.

(56) References Cited

U.S. PATENT DOCUMENTS

| | | | | |
|---|---|---|---|---|
| 590,280 | A * | 9/1897 | Rockstroh | 279/23.1 |
| 719,017 | A * | 1/1903 | Lenhardtson | 132/328 |
| 2,016,597 | A * | 10/1935 | Drake | 601/141 |
| 2,184,105 | A | 12/1937 | Steirer | |
| 2,442,503 | A * | 6/1948 | Melnikoff | 132/320 |
| 2,510,194 | A * | 6/1950 | Thomas | 132/325 |
| 2,648,906 | A | 1/1951 | Halms | |
| 3,581,399 | A * | 6/1971 | Dragan | 433/90 |
| 3,771,537 | A * | 11/1973 | Schole | 433/142 |
| 3,943,628 | A | 3/1976 | Kronman et al. | |
| 4,372,331 | A * | 2/1983 | Thompson | 132/320 |
| 4,696,646 | A | 9/1987 | Maitland | |
| 4,778,385 | A | 10/1988 | Herrin | |
| 4,913,176 | A * | 4/1990 | DeNiro | 132/329 |
| 5,030,093 | A | 7/1991 | Mitnick | |
| 5,061,179 | A | 10/1991 | Dragan | |
| 5,151,029 | A * | 9/1992 | Levy | 433/29 |
| 5,346,394 | A | 9/1994 | DeStefanis | |
| 5,743,738 | A | 4/1998 | Baffelli et al. | |
| 5,890,630 | A * | 4/1999 | Lobdell | 222/192 |
| 6,022,217 | A | 2/2000 | Hugo | |
| 6,074,210 | A | 6/2000 | Garrison | |
| 6,254,393 | B1 | 7/2001 | Hugo | |
| 6,511,321 | B1 | 1/2003 | Trushkowsky et al. | |
| 6,524,103 | B1 | 2/2003 | Winkler et al. | |
| 6,913,464 | B2 | 7/2005 | Maissami | |
| 6,929,475 | B1 | 8/2005 | Dragan | |
| 6,976,842 | B1 | 12/2005 | Miggantz | |
| 7,425,130 | B2 | 9/2008 | Schaffner et al. | |
| 2005/0282102 | A1 * | 12/2005 | Kert | 433/29 |
| 2006/0147875 | A1 | 7/2006 | Ahn | |
| 2011/0027753 | A1 | 2/2011 | Maurat et al. | |

* cited by examiner

*Primary Examiner* — Yogesh Patel
(74) *Attorney, Agent, or Firm* — Ira S. Dorman

(57) ABSTRACT

The device includes a shim component constructed for use in the non-surgical treatment of interproximal carious dental lesions. A plunger may be provided for driving substances through a tube-like channel or bore in the shim component, or an electromagnetic energy-transmissive material may fill the channel, in either case for delivering to the site of the lesion a medium that is effective for directly or indirectly killing, or biologically damaging, the carious bacteria.

6 Claims, 3 Drawing Sheets

INTERPROXIMAL NON-SURGICAL CARIES TREATMENT DEVICE AND METHOD

CROSS-REFERENCE TO RELATED APPLICATION

This application claims the benefit of U.S. Provisional Patent Application No. 61/572,711, filed Jul. 20, 2011, the entire specification of which is incorporated hereinto by reference.

BACKGROUND OF THE INVENTION

Dental caries occur on all surfaces of teeth, and carious lesions can, and do, form between teeth in areas that are inaccessible directly for treatment; these are termed "interproximal" caries or carious lesions. Because these carious lesions are between the teeth, access generally requires the physical removal, with a dental drill, of sound tooth structure over and/or proximate the lesion so as to, in turn, permit physical removal of the decay.

Carious bacteria can be entombed, or sealed, within conventional acrylic dental resins to thereby cause the death of the bacteria by isolating it from the source of its needed nutrients, i.e., food debris. But access to the carious lesion, to permit the application of such a seal, typically also requires the physical destruction of sound tooth structure.

Alternatively, carious bacteria can be entombed within deposits of laser-ablated tooth enamel and dentin. While any removal of sound tooth structure will usually be undesirable, enamel and dentin damaged by ablation can often be repaired by remineralization, through topical fluoride treatments. As yet another technique, carious bacteria can be killed by exposure to sufficient doses of microwave energy, to which tooth enamel is translucent. Laser beam radiation is also effective for killing carious bacteria directly.

BRIEF SUMMARY OF THE DISCLOSURE

Accordingly, broad objects of the present invention are to provide a novel device and method for treating interproximal dental caries.

More specific objects of the invention are to provide such a device and method wherein and whereby treatment of interproximal dental caries can be effected without substantial destruction of sound tooth structure lying over, or located proximate to, the carious lesion.

Another object of the invention is to provide such a device which may include means for driving substances and materials to the site of an interproximal carious lesion.

Still another object of the invention is to provide such a device that includes an element for efficiently transmitting, to the site of an interproximal carious lesion, electromagnetic energy that is effective for directly or indirectly killing, or biologically damaging, infecting bacteria.

Additional objects of the invention are to provide such a device which is of incomplex and inexpensive construction, and which is facile and effective for use to treat interproximal dental caries.

It has now been found that certain of the foregoing and related objects of the invention are attained by the provision of a device for treating interproximal dental caries, comprised of a hard, rigid, generally flat shim of such thickness, between opposite side surfaces, as to permit its insertion longitudinally between two adjacent teeth. The shim has a top at one end and a bottom portion that terminates in a sharp edge at an opposite end. The bottom portion is formed with a bevel surface, on one of the opposite sides of the shim, leading to the sharp edge. A generally longitudinal tube-like channel or bore extends from the top of the shim to the bevel surface, for enabling the delivery, from the entrance of the channel substantially at the top (inclusive of extending through the top surface) to its exit on the bevel surface, of a carious lesion-treating medium (i.e., one or more substances, or electromagnetic energy).

In certain embodiments of the device the channel of the shim will be normally empty. Preferably, in those embodiments, a cavity will be formed into the bevel surface at the exit end of the channel, and most desirably at least a lower section of such a cavity will be defined by a sharp peripheral edge, lying on the bevel surface.

The treating device of this embodiment will also preferably include a plunger having a stem that is dimensioned and configured for being introduced into the entrance end of the shim channel, and for slideable engagement therein. The plunger will function to effectively drive a substance (e.g., a liquid, or a mobile pasty or semi-solid material) contained in the channel to its exit end.

In other embodiments of the treating device, the channel of the shim will be filled with a solid, electromagnetic energy-transmissive material. Such a material will usually be either a glass that is capable of transmitting a laser beam, or a synthetic resinous material (e.g., a hard acrylic resin) that is capable of transmitting microwave energy.

The shim itself will normally be fabricated from either a hard, rigid synthetic resinous material (e.g., nylon, Teflon, polycarbonate, etc.), or from a metal having the same qualities (e.g., stainless steel, titanium, etc.). The material of fabrication will be selected so as to substantially avoid chemical or electromagnetic interaction, as the case may be, with the medium (i.e., the substance or energy) that is delivered through the shim channel.

Other objects of the invention are attained by the provision of a method for treating an interproximal carious dental lesion, comprising steps:

providing a device comprised of a hard, rigid, generally flat shim, as hereinabove and hereinafter described;

inserting the shim between two adjacent teeth with its sharp edge leading, one tooth of the pair having a carious lesion on an interproximal surface thereof;

adjusting the position of the shim, as necessary, to substantially align the exit end of the longitudinal channel of the shim with the carious lesion to be treated;

introducing into the entrance end of the shim channel a medium that is directly or indirectly effective to kill, or metabolically damage, carious bacteria infecting the lesion;

delivering the lesion-treating medium to the exit end of the channel and, thereby, to the site of the carious lesion; and thereafter withdrawing the shim from between the teeth.

In certain embodiments of the method of the invention, the shim channel will be normally empty and a liquid substance (e.g., an acid) will be delivered therethrough to the carious lesion site, to etch the surface of the lesion. The etching step will normally be followed by a water-flush step (also effected through the channel of the shim), and thereafter by a step of introducing into the channel entrance, for delivery to the lesion site, a mobile dental filling or repair material (e.g., a conventional acrylic resin) that is curable (typically by UV radiation) to a solid state; preferably, a plunger will be employed for driving the dental filling material to the lesion site. In instances in which a lower section of a cavity formed into the bevel surface of the shim is defined by a sharp peripheral edge, withdrawal of the shim, longitudinally from between the teeth, will cause the sharp edge to excise excess cured dental material that may overlie or extend beyond the proximate tooth surface. A step for curing or hardening of the filling/repair material will normally be effected, or be permitted to occur, prior to shim withdrawal.

In other embodiments of the method, the channel of the shim employed will be filled with a solid, electromagnetic energy-transmissive material. In carrying out the method, radiation will be directed into the channel entrance for transmission and delivery, via the energy-transmissive material, to the carious lesion site so as to directly or indirectly kill or destroy the infecting bacteria. The electromagnetic energy utilized will generally be either that of a laser beam or microwave radiation. In such embodiments, the shim will be fabricated from a material that will not substantially attenuate the electromagnetic energy during its transmission.

DETAILED DESCRIPTION OF THE INVENTION

Figure 2:
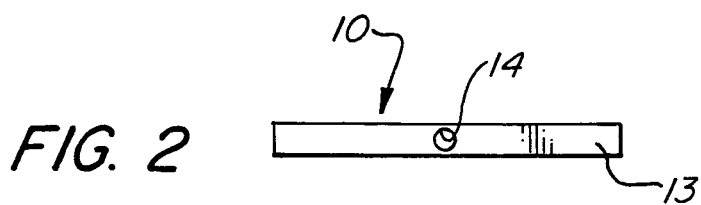
FIG. 2 is a plan view of the shim component of FIG. 1.
Figure 1:
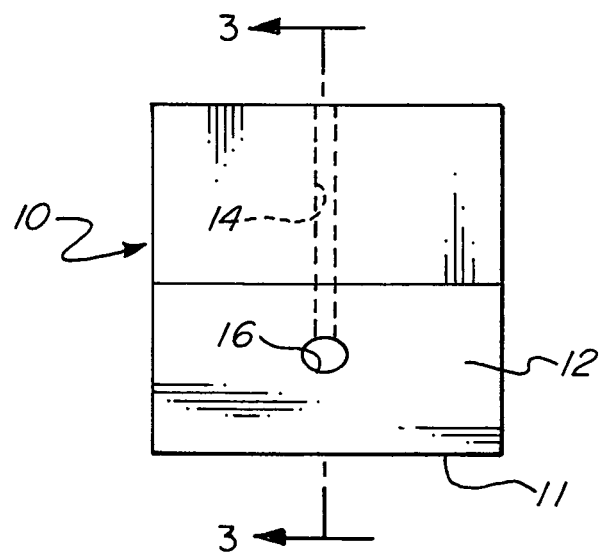
FIG. 1 of the drawings is a front elevational view of a shim component comprising a first device embodying the present invention.
Figure 3:
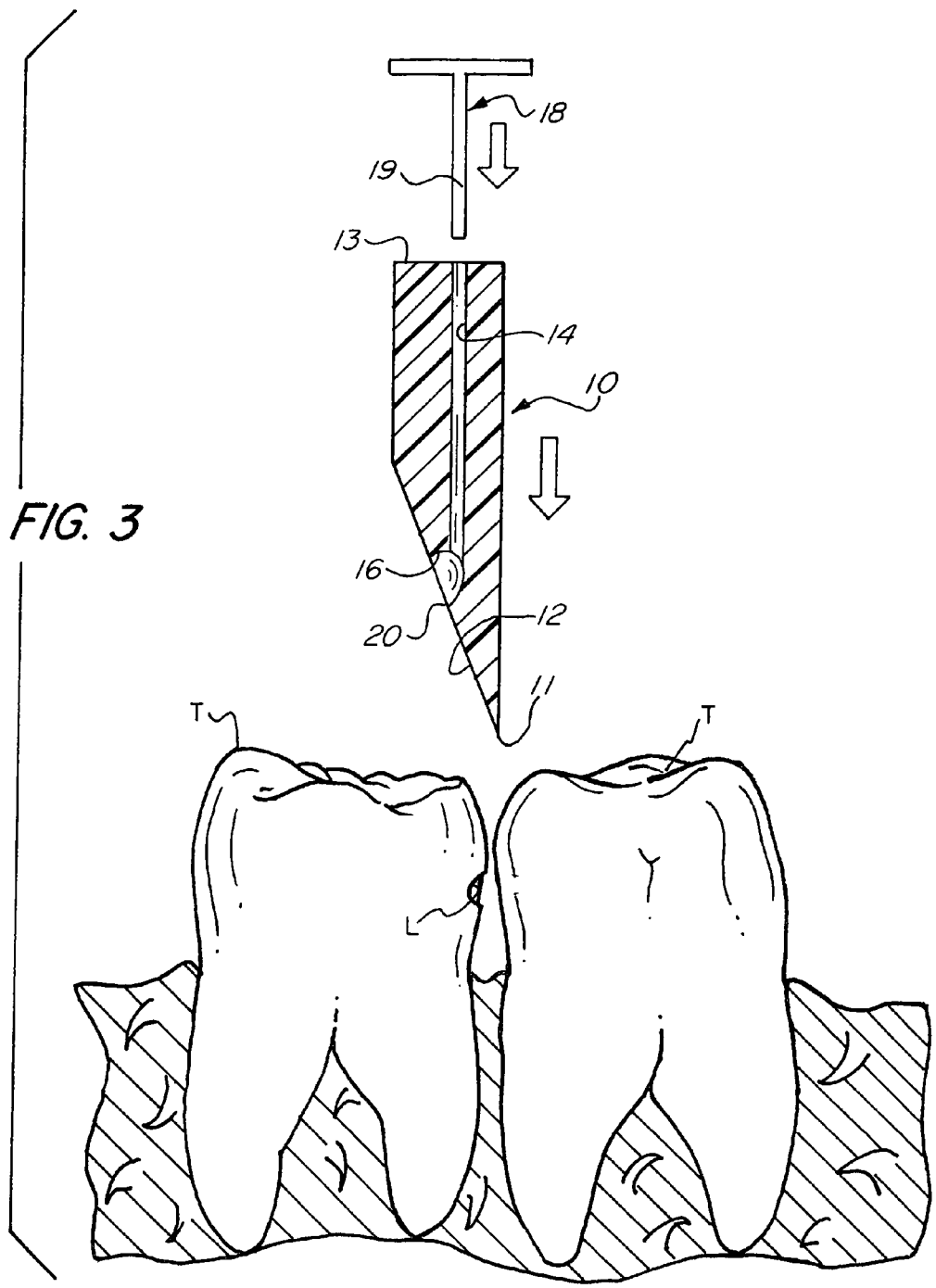
FIG. 3 is a diagrammatic illustration showing a device embodying the invention in use for treatment of an interproximal carious lesion, wherein the device includes the shim component of FIGS. 1 and 2, taken in section along line 3-3 of FIG. 1 and drawn to a scale greatly enlarged therefrom, in combination with a plunger component.

Turning now in detail to FIGS. 1 through 3 of the appended drawings, the device illustrated comprises a flat plastic shim component, generally designated by the number 10, having a sharp edge 11 at the bottom, to which a beveled or inclined surface 12 leads. The shim component 10 is formed to contain a very small diameter channel or bore 14 that extends generally longitudinally from the top 13 of the shim component 10 to the bevel surface 12; a reservoir cup or cavity 16 is formed at the lower end of the channel 14, on the bevel surface 12 and extending thereinto.

To treat the interproximal carious lesion L, the sharp edge 11 of the shim component 10 is inserted between the adjacent teeth T, and is forced downwardly (or upwardly, as the case may be) so as to position the reservoir cup 16 substantially directly against the lesion L. The pre-insertion aligned position of the shim component 10 is depicted in FIG. 3.

Prior to insertion of the shim, the interproximal surfaces of teeth T are cleaned, and plaque is removed with dental floss. The lesion L is diagnosed, and its precise position ascertained by dental bitewing radiographs. It will be appreciated that wedges and other devices may be used to assist insertion and positioning of the shim, such as to spread the teeth and/or depress or deflect gingival tissue, as will be evident to those skilled in the art.

As can be seen, the channel 14 opens at the top 13 of the shim component 10 and leads to the reservoir cup 16. After insertion, the channel 14 is filled with an acid (e.g., hydrofluoric, hydrochloric, or phosphoric) to etch the surface of the lesion L. The acid may be forced into the reservoir cup 16 by use of the small plunger component, shown in FIG. 3 and generally designated by the number 18, the stem 19 of which is inserted from the top and is slideably received in the channel 14. The amount of treatment chemical used is minute because the surface lesion L will typically be very small, and any substantial treatment of proximate sound tooth structure is unnecessary, unwarranted, and undesirable.

After etching has been completed, the shim channel 14 is filled with water; the plunger 18 is used to force the water into the cup 16 so as to flush the channel and the lesion L and to rinse away the acid. The channel 14 is then dried with compressed air, and filled with a mobile, light-curing (e.g., by UV radiation) tooth-filling or repairing acrylic resin, which is also forced into the cup 16 by manipulation of the plunger 18. The resin filling is then cured to hardness. It will be appreciated that, in this instance, the shim 10 is fabricated from a synthetic resinous material that is capable of effectively and efficiently transmitting the cure-initiating radiation so as to ensure that the dose reaching the site is sufficient to effect full curing to hardness, under practical operating conditions.

The shim 10 is thereafter removed longitudinally from between the teeth T. Due to the presence of the sharp element 20 defining the lower peripheral edge of the reservoir cup 16 on the bevel surface 12, withdrawal of the shim will, as an inherent consequence, cause the element 20 to excise residual flash or excess deposit of the cured resin that may overlie or protrude beyond the proximate tooth surface. As a final step, dental floss will be snapped between the teeth T to check for any additional excess resin that may have been missed during withdrawal of the shim component, which excess resin can be removed using a scalpel blade.

Figure 5:
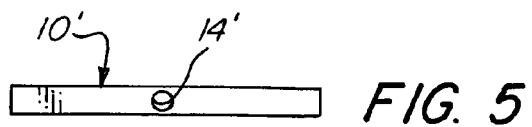
FIG. 5 is a plan view of the shim component of FIG. 4.
Figure 4:
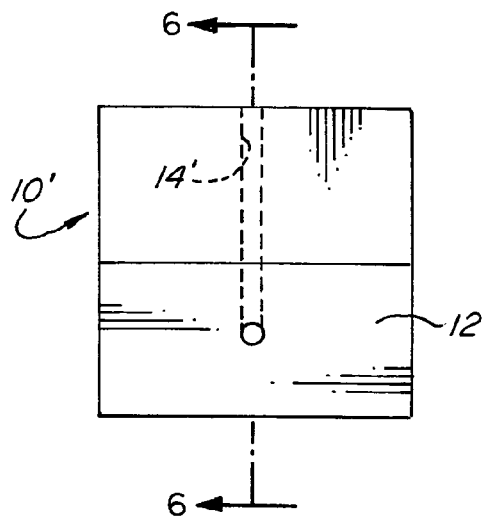
FIG. 4 is a front elevational view of a shim component comprising a second device embodying the present invention.
Figure 6:
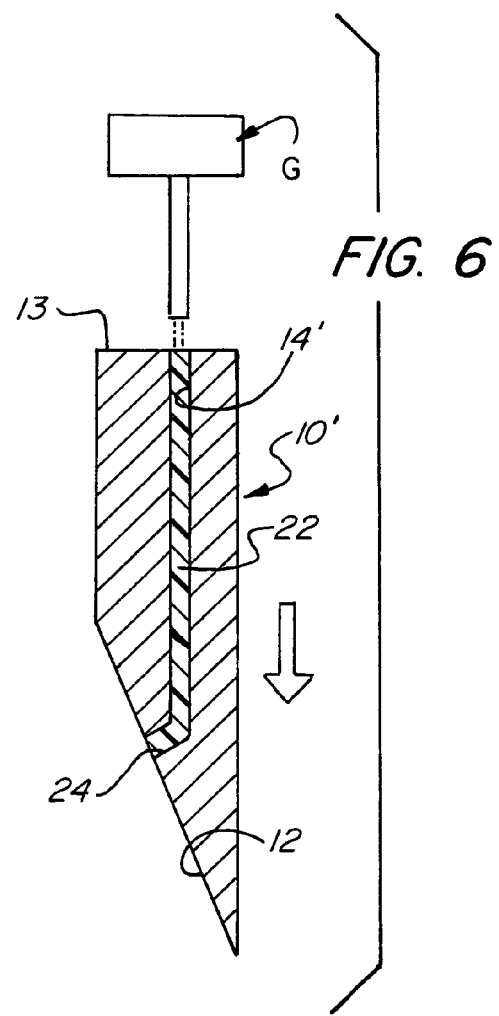
FIG. 6 is a diagrammatic illustration showing a system for treatment of carious lesions utilizing the shim component of FIGS. 4 and 5, drawn to a scale greatly enlarged therefrom and showing the shim component taken in section along lines 6-6 of FIG. 4, the system depicted additionally including a radiation source component.

Turning now to in detail to FIGS. 4 through 6 of the drawings, therein illustrated is a second form of shim component embodying the invention and generally designated by the numeral 10'; in this instance the shim 10' is shown to be of metal fabrication. As can be seen, a channel 14' extends from the top 13 of the shim 10' and exits on the bevel surface 12, being curved however at its lower end to take a slight jog to the surface 12 (an alternative channel construction could consist of two straight sections, with a reflective element at the intersection). The channel 14' is filled with a solid, electromagnetic energy-transmitting material 22.

Associated with the shim 10' is, as seen in FIG. 6, a radiation generator, generally designated G. The generator G produces a beam of electromagnetic radiation, and projects it (with suitable focusing) toward the entrance end of the bore 14', from which the energy is transmitted, through the solid material 22, to the exit end 24.

In use, the shim of this embodiment is inserted between adjacent teeth in the manner hereinabove described in connection with the first embodiment of the invention illustrated, with particular reference to FIG. 3, and with the same pre-insertion measures being taken. In this instance, the inserted shim 10' is optimally so positioned as to locate the exit end 24 of the solid element 22 directly against the carious lesion L.

After being effectively positioned relative to the shim 10', the generator G is brought into operation to generate a beam of energy for transmission to the site of the lesion, as the functional medium for producing the desired treatment effect. As previously disclosed herein, the generator will normally produce a laser beam or a beam of microwave energy, either of which is effective for directly killing or destroying infecting bacteria of a carious lesion, but with laser beams being additionally effective for starving the bacteria through entombment under or within ablated tooth enamel and dentin. Upon completion of the irradiation step, the shim 10' is removed from between the teeth, and any final steps necessary to complete the treatment are taken.

As previously described, the shim component will be constructed of any suitable hard, rigid material that is capable of being formed with a relatively sharp leading edge adapted for initiating entry between adjacent teeth, and that is suited for use for the delivery of substances or radiant energy, or both. Although, in the specific embodiments described and depicted, the shim component is a flat, essentially square piece, it will be appreciated that variations of shape may be incorporated without departure from the scope of the appended claims. For example, the shim may have a slight curvature in its transverse configuration (such as to better conform to tooth surfaces), its lateral margins may converge toward one another and/or be nonlinear, and other modifications that will occur to those skilled in the art may be incorporated as well. Although the shim will typically be about 20 mm square and about 0.5 mm thick (between its opposite side surfaces, above of the bevel), it may of course have different dimensions; moreover, a single form of shim may be provided in each of several sizes.

In those instances in which the channel of the shim is filled with an element of energy-transmissive material, the particular composition of the element will of course depend upon the nature of the electromagnetic energy that is to be used. As indicated above, for example, when the energy employed is provided by a laser beam the bore may contain a glass fiber optic filament; when microwave energy is utilized, the solid core may be a clear, hard acrylic resin. It should be appreciated that other forms and wavelengths of electromagnetic energy may be effective for killing, destroying, or disabling carious bacteria, and/or for encapsulating the bacteria within or under ablated dental materials. Provided that the composition of the channel core element is suitably selected, and that the shim is otherwise appropriately constructed, it is anticipated that such other forms and wavelengths of radiation will find utility in the practice of the present invention.

The composition that will be desirable for fabrication of the shim will, as indicated above, depend upon the nature of the medium that is to be used for treatment of the carious lesion, as will be evident to those skilled in the art in light of the present disclosure. It will also be evident that the nature of any dental filling or repair material employed will influence the choice of shim body composition as well. Needless to say, if a filling material used is one that is cured through a photoinitiated reaction, the shim body must be fabricated, entirely or in significant part, of a resin that is transmissive of corresponding wavelengths of energy. On the other hand, if an opaque resin or metal shim body is preferred, materials that harden through other mechanisms (e.g., catalysis, chemical interactions, etc.) can be employed.

Any appropriate technique may be used to fabricate the shims, including punching, drilling, grinding, milling, other machining operations, molding, etc. Due to the small cross-sectional dimensions of the bore or channel within the shim body, however, a most practical way to form it may involve the initial cutting of a slot into the beveled side of the shim, extending from the top of the shim to its bevel surface, and then closing the slot, to produce the desired channel, by securing a strip of material on lands or shoulders milled along the slot on its opposite sides. If the channel is to contain a solid resin for transmitting electromagnetic radiation, a preformed element thereof (e.g., a fiber optic filament) or a polymerizable liquid formulation, would of course be deposited in the slot before any covering piece is put in place.

Thus, it can be seen that the present invention provides a novel device for treating interproximal dental caries, and a novel method for effecting such treatment utilizing the device, whereby substantial destruction of sound tooth structure lying over, or located proximate to, a carious lesion is avoided. The device may include means for driving substances to the site of an interproximal carious lesion, or it may include an element for efficiently transmitting, to the site, electromagnetic energy that is effective for directly or indirectly killing, or biologically damaging, infecting bacteria. The device is of incomplex and inexpensive construction, and it is facile and effective for use for its intended purposes.

Having thus described the invention, what is claimed is:

1. A device for treating interproximal dental caries comprising a hard, rigid, generally flat shim of such thickness between opposite side surfaces as to permit its insertion longitudinally between two adjacent teeth;

said shim having a top at one end and a bottom portion that terminates in a sharp and elongated edge at an opposite end;

said bottom portion being formed with a bevel surface on one of said opposite sides, leading to and extending along said sharp and elongated edge;

said shim having a generally longitudinal channel therein that extends from an entrance end at the top of said shim to an exit end on said bevel surface for enabling delivery, from said top directly to said bevel surface, of a caries treating medium; and said shim having a cavity formed into said bevel surface at said exit end of said channel.

2. The device of claim 1 wherein at least a lower section of said cavity is defined by a sharp peripheral edge lying on said bevel surface.

3. A device for treating interproximal dental caries comprising a hard, rigid, generally flat shim of such thickness between opposite side surfaces as to permit its insertion longitudinally between two adjacent teeth;

said shim having a top at one end and a bottom portion that terminates in a sharp and elongated edge at an opposite end;

said bottom portion being formed with a bevel surface on one of said opposite sides, leading to and extending along said sharp and elongated edge;

said shim having a generally longitudinal channel therein that extends from an entrance end at the top of said shim to an exit end on said bevel surface for enabling delivery, from said top directly to said bevel surface, of a caries treating medium; and said device additionally including a plunger having a stem dimensioned and configured for being introduced into said entrance end of said channel and for slideable engagement therein, whereby said plunger can function to drive a substance contained in said channel to said exit end thereof.

4. A device for treating interproximal dental caries comprising a hard, rigid, generally flat shim of such thickness between opposite side surfaces as to permit its insertion longitudinally between two adjacent teeth;

said shim having a top at one end and a bottom portion that terminates in a sharp and elongated edge at an opposite end;

said bottom portion being formed with a bevel surface on one of said opposite sides, leading to and extending along said sharp and elongated edge;

said shim having a generally longitudinal channel therein that extends from an entrance end at the top of said shim to an exit end on said bevel surface for enabling delivery, from said top directly to said bevel surface, of a caries treating medium; and said channel being filled with a solid, electromagnetic energy-transmissive material.

5. The device of claim 4 wherein said energy-transmissive material is a glass material capable of transmitting a laser beam.

6. The device of claim 4 wherein said material is a synthetic resinous material capable of transmitting microwave energy.

* * * * *